United States Patent
Lo et al.

(10) Patent No.: US 8,821,159 B2
(45) Date of Patent: Sep. 2, 2014

(54) DENTAL IMPLANT GUIDING DEVICE

(75) Inventors: Kai-Szu Lo, Kaohsiung (TW); Yauchia Liu, Kaohsiung (TW); Ching-Chieh Huang, Kaohsiung (TW); Hsien-Nan Kuo, Kaohsiung (TW)

(73) Assignee: Metal Industries Research and Development Center, Kaohsiung (TW)

( * ) Notice: Subject to any disclaimer, the term of this patent is extended or adjusted under 35 U.S.C. 154(b) by 83 days.

(21) Appl. No.: 13/619,414

(22) Filed: Sep. 14, 2012

(65) Prior Publication Data

US 2013/0157219 A1 Jun. 20, 2013

(30) Foreign Application Priority Data

Dec. 16, 2011 (TW) .............................. 100146685 A

(51) Int. Cl.
*A61C 3/02* (2006.01)
(52) U.S. Cl.
USPC ........................................................... 433/76
(58) Field of Classification Search
USPC ............. 433/72, 75, 76; 606/96; 33/513, 514
See application file for complete search history.

(56) References Cited

U.S. PATENT DOCUMENTS

| 5,302,122 | A * | 4/1994 | Milne | 433/76 |
| 6,319,000 | B1 * | 11/2001 | Brannemark | 433/75 |
| 2011/0275032 | A1 * | 11/2011 | Tardieu et al. | 433/174 |
| 2013/0017507 | A1 * | 1/2013 | Moffson et al. | 433/27 |

* cited by examiner

*Primary Examiner* — Sunil K Singh
(74) *Attorney, Agent, or Firm* — Muncy, Geissler, Olds & Lowe, P.C.

(57) ABSTRACT

A dental implant guiding device is applied in guiding the drill of the drilling apparatus in different dimensions. The device includes a guiding module and a guiding seat. The guiding module contains at least one guiding unit where a sleeve with a cavity is disposed. A guiding hole and a guiding slot, where an opening at a fringe of the guiding unit is defined, are disposed at two sides of the sleeve. The guiding seat forms a first hole. At two sides of the first hole, a first guiding shank and a second guiding shank respectively corresponding to the guiding hole and the guiding slot are disposed. The second guiding shank slides into the guiding slot, which allows the first guiding shank inserting into the guiding hole for the drill to position at the center of the cavity of the sleeve, thereby achieving the fast positioning and friction reduction.

5 Claims, 11 Drawing Sheets

DENTAL IMPLANT GUIDING DEVICE

BACKGROUND OF THE INVENTION

1. Field of the Invention

The present invention relates to a guide device, in particular to a dental implant guiding device that is convenient to doctors in surgery.

2. Description of the Related Art

For the accuracy of the drilling orientation in dental implant, a surgical guiding plate is prefabricated to co-operate the teeth construction of the patients. A fixed sleeve is disposed on the surgical guiding plate, and then the doctor holds a drilling apparatus with the drill and places the drill into the fixed sleeve to proceed drilling. Wherein, when the diameter of the fixed sleeve is larger than the diameter of the drilling, the drill easily deviates from its original position while drilling, which results in the inaccuracy of the drilling orientation. If the dimensions of the fixed sleeve and the drill are over closed, the friction formed between the drill and the inner fringe of the fixed sleeve would cause the motor of the drilling apparatus to be damaged, the drill to be overheated, and the debris resulted from the friction to be dropped in the surgical area. Therefore, the fixed sleeve requires replacements according to different sizes of the drills, which is inconvenient in using.

To improve the problem of the frequent replacements in light of different sizes of the drills, a prior patent publication number 2010/0004698 whose title is "METHOD FOR PRODUCING A BONE PROSTHESIS OR A PRE-IMPLANT SIMULATION, AND EQUIPMENT USED" is disclosed. The method comprises a guiding unit and a guiding seat; wherein, the guiding unit is disposed on the surgical guiding plate. A through hole is defined on the guiding unit, and two guiding holes are respectively defined at two sides of the through hole. The guiding seat is sleeved on the drilling apparatus, and the drill is extended out of the guiding seat. Two guiding shanks that can place into the corresponding guiding holes are respectively disposed on the guiding seat. The drill is positioned by inserting the guiding shanks into the guiding holes so that the friction due to the deviation of the drilling head can be prevented. Moreover, the diameter of the through hole of the guiding unit needs not change according to the sizes of the drilling head.

The sizes of the guiding shanks and the guiding holes are small and hard to aim accurately. The dimensions of the guiding unit is larger and the space of the rear teeth of the patient is smaller, so the guiding shank is much difficult to aim and insert to the guiding hole, and the drilling process becomes harder.

Referring to the Taiwan patent number M348588 issued by "tooth mold construction, dental implant device, and dental implant system" is disclosed. This prior patent discloses a dental guiding device which prefabricates two guiding holes out of the drilling hole of the tooth mold and two guiding shanks of the drill apparatus disposed at the outer fringe of the drilling hole. When the drill inserts into the drilling hole, the guiding shanks respectively penetrate through the guiding holes so as to position the drill for proceeding the drilling.

Because of the construction of the prefabricated guiding holes on the tooth mold, the gums would be pricked if the guiding shanks are too long, In contrast, if the guiding shanks are too short, the guiding effect would not happen. Moreover, the small sizes of the guiding shanks and the guiding holes are still difficult to aim with each other accurately.

SUMMARY OF THE INVENTION

It is therefore the main purpose of this invention to provide a dental implant guiding device, which improves the problem of hardly aiming accurately deriving from cooperating the guiding shanks with the guiding holes of the conventional guiding device.

The secondary purpose of this invention is to provide a dental implant guiding device, which improves the problem of the friction between the drill and the inner wall of the sleeve in surgery.

The dental implant guiding device in accordance with the present invention, which guides the drill of the drilling apparatus, comprises:

a guiding module which comprises at least one guiding unit; wherein, a sleeve with a cavity is disposed on the guiding unit, a guiding hole and a guiding slot are respectively disposed at two sides of the sleeve. The guiding slots forms an opening at the outer fringe of the guiding unit defines; and a guiding seat disposed on the drilling apparatus for the drill to insert and orientate in the sleeve. The guiding seat has a first hole for allowing the drill to penetrate therethrough. A first guiding shank corresponding to the guiding hole and a second guiding shank corresponding to the guiding slot are disposed at two sides of the first hole. A length of the second guiding shank is longer than a length of the first guiding shank.

When the drill inserts into the cavity of the sleeve and the guiding seat sleeves on the drilling apparatus, the second guiding shank of the guiding seat easily slides in the guiding slot. After the second guiding shank is positioned, the first guiding shank inserts in the corresponding guiding hole. The guiding hole restrains the first guiding shank from slanting, and the guiding slot restrains the guiding seat from rotating about the first guiding shank as the center so that the drill is positioned in the middle of the sleeve, and the dental implant guiding device is adapted to different dimensions of drills without replacing the guiding unit. The sleeve of the guiding unit provides a larger cavity. By the combinations of the guiding hole and the first guiding shank as well as the guiding slot and the second guiding shank, the drill is positioned in the sleeve to prevent the apparatus from being broken by the friction formed between the drill and the sleeve. The second guiding shank laterally slides in the guiding slot for initially attaining a rapid placement and position, which facilitates a quick connection of the guiding module with the guiding seat for benefiting the surgery when the first guiding shank is accurately placed in the guiding hole.

DETAILED DESCRIPTION OF THE PREFERRED EMBODIMENTS

Figure 1:
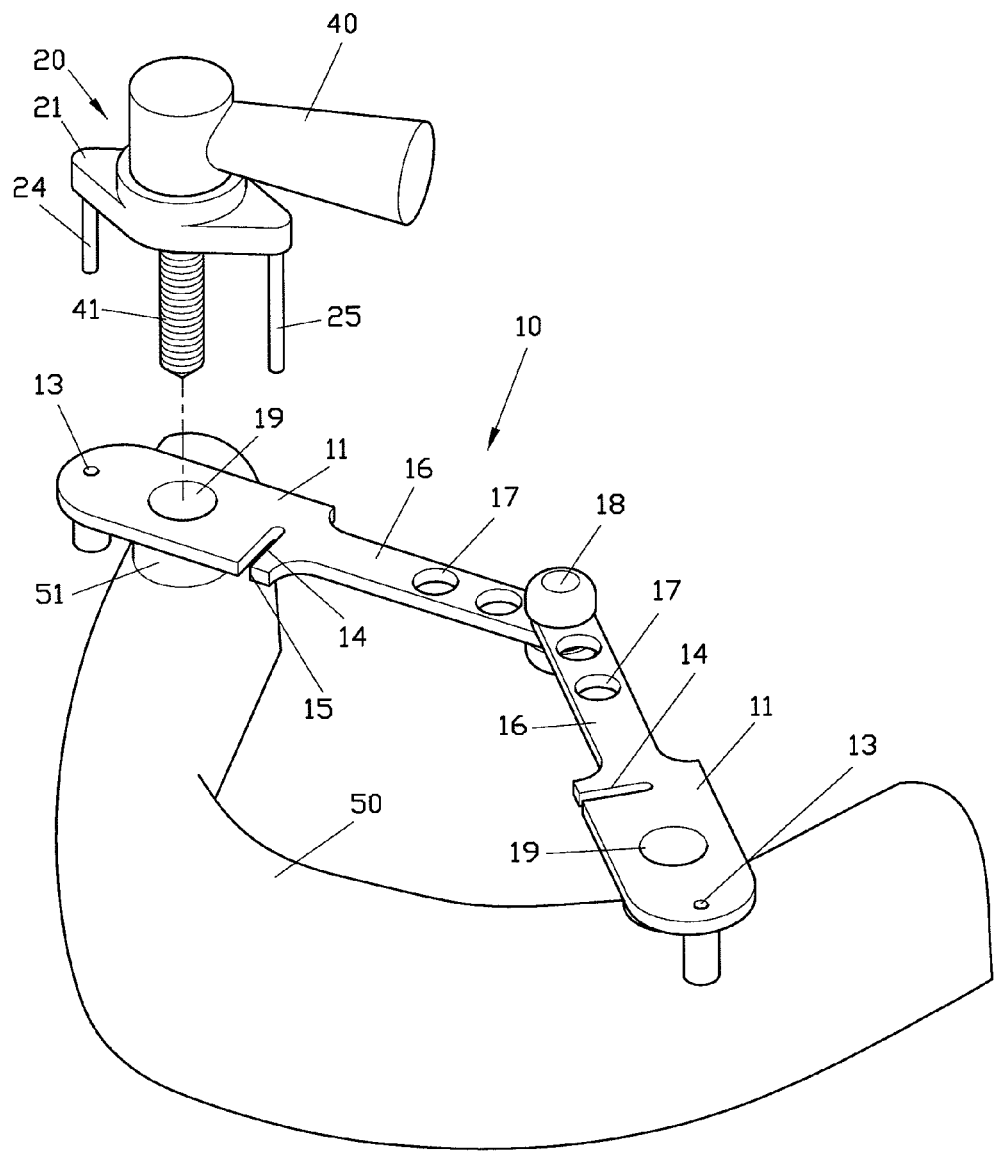
FIG. 1 is a perspective view showing a first preferred embodiment of the present invention.
Figure 2:
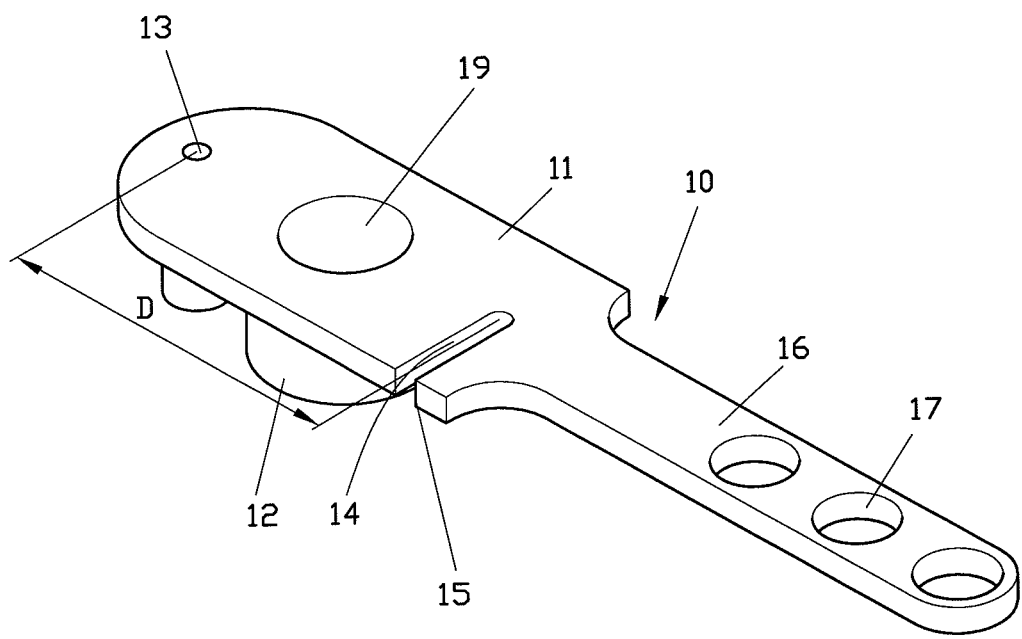
FIG. 2 is a perspective view showing a guiding unit of the first preferred embodiment of the present invention.
Figure 3:
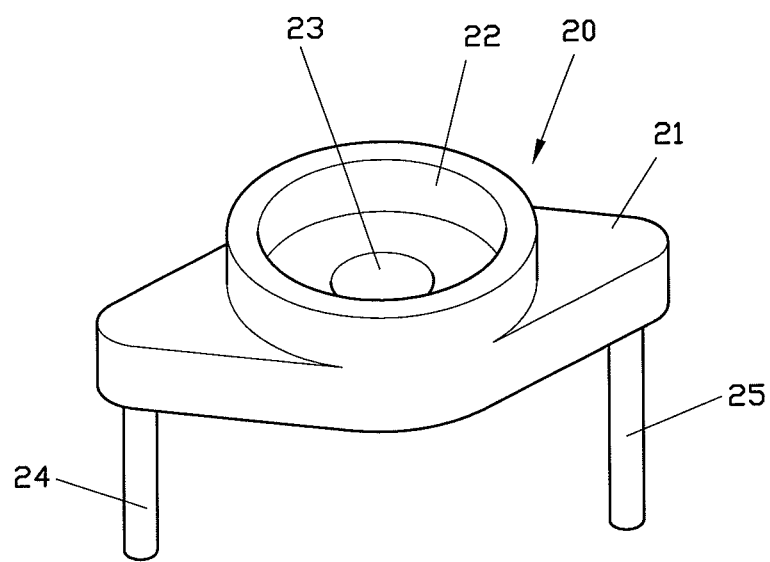
FIG. 3 is a perspective view showing a guiding seat of the first preferred embodiment of the present invention.

Referring to FIGS. 1, 2, and 3, a first preferred embodiment of the present is shown. The dental implant guiding device which is used to guide a drill 41 of a positioned drilling apparatus 40 for drilling the gums in the oral cavity comprises a guiding module 10 and a guiding seat 20.

Figure 4:
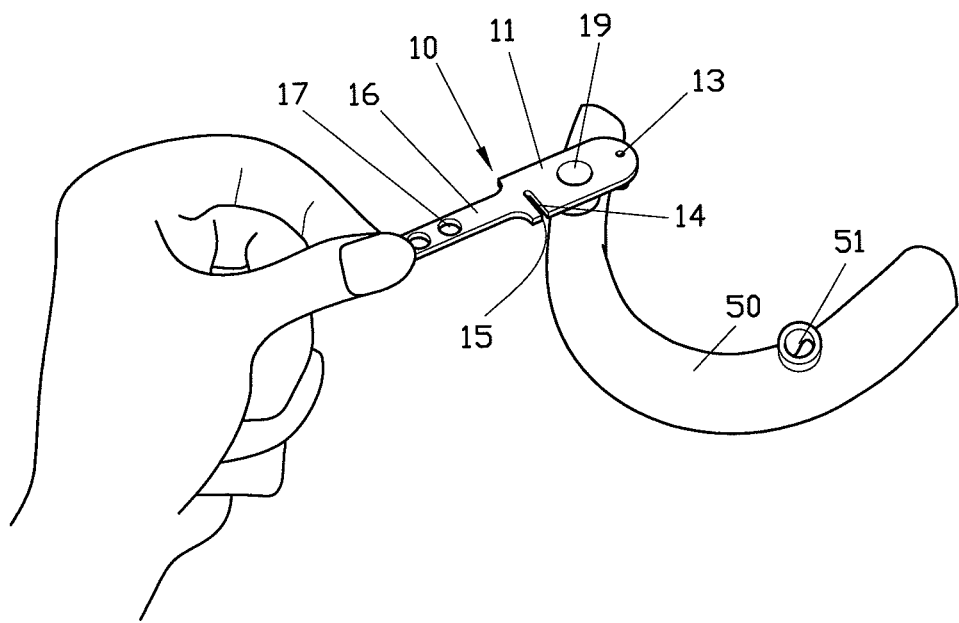
FIG. 4 is a schematic view showing a single guiding unit of the first preferred embodiment of the present invention in use.
Figure 5:
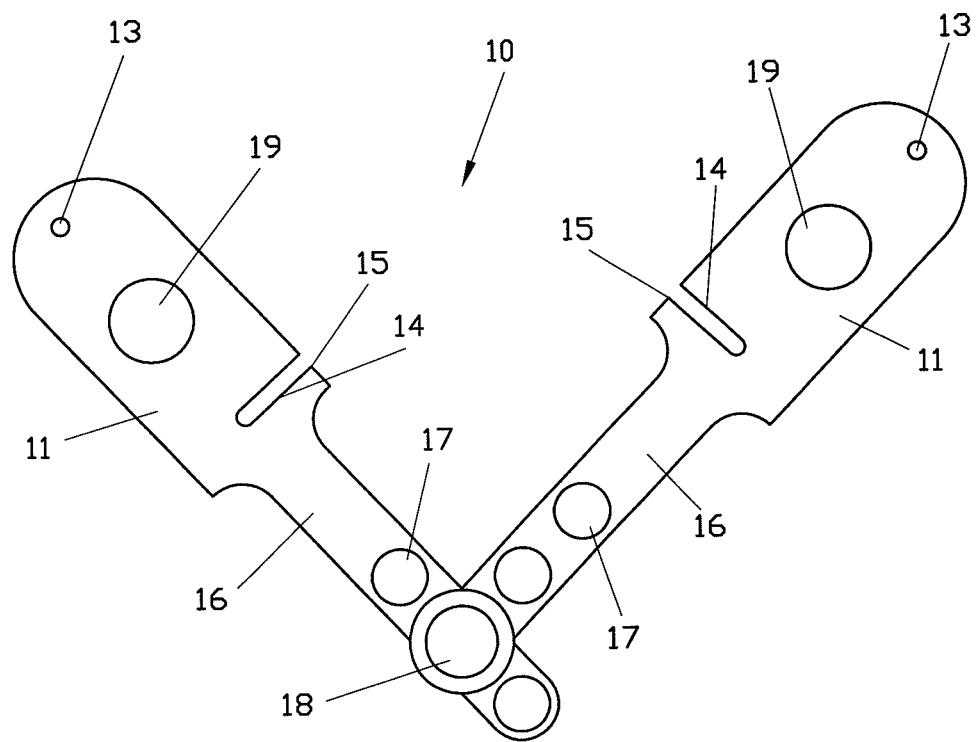
FIG. 5 is a perspective view showing a guiding module of the first preferred embodiment of the present invention.

The guiding module 10 contains at least one guiding unit 11; wherein, a sleeve 12 is disposed on the guiding unit 11. The sleeve 12 has a cavity 19, and a guiding hole 13 and a guiding slot 14 are disposed at two sides of the sleeve 12, respectively; wherein, the guiding slot 14 forms an opening 15 defined at the outer fringe of the guiding unit 11. Preferably, the guiding slot 14 is a straight slot. Preferably, a side (or a closed side) opposite to the opening 15 of the guiding slot 14 is defined as an arc shape, and a center of the arc is aligned with a center of the sleeve 12 (or the cavity 19) and a center of the guiding hole 13. In the first preferred embodiment of the present invention, a shaft 16 is disposed on the guiding unit 11, and the guiding slot 14 is defined between the sleeve 12 and the shaft 16. Referring to FIG. 4, the guiding module 10 contains a guiding unit 11. Referring to FIG. 5, the guiding module 10 contains a plurality of guiding units 11, each of which includes at least one combination hole 17 disposed on the shaft 16, whereby a combination unit 18 is inserted into the corresponding combination holes 17 of the guiding units 11 to pivotally join the plurality of the guiding units 11.

Figure 7A:
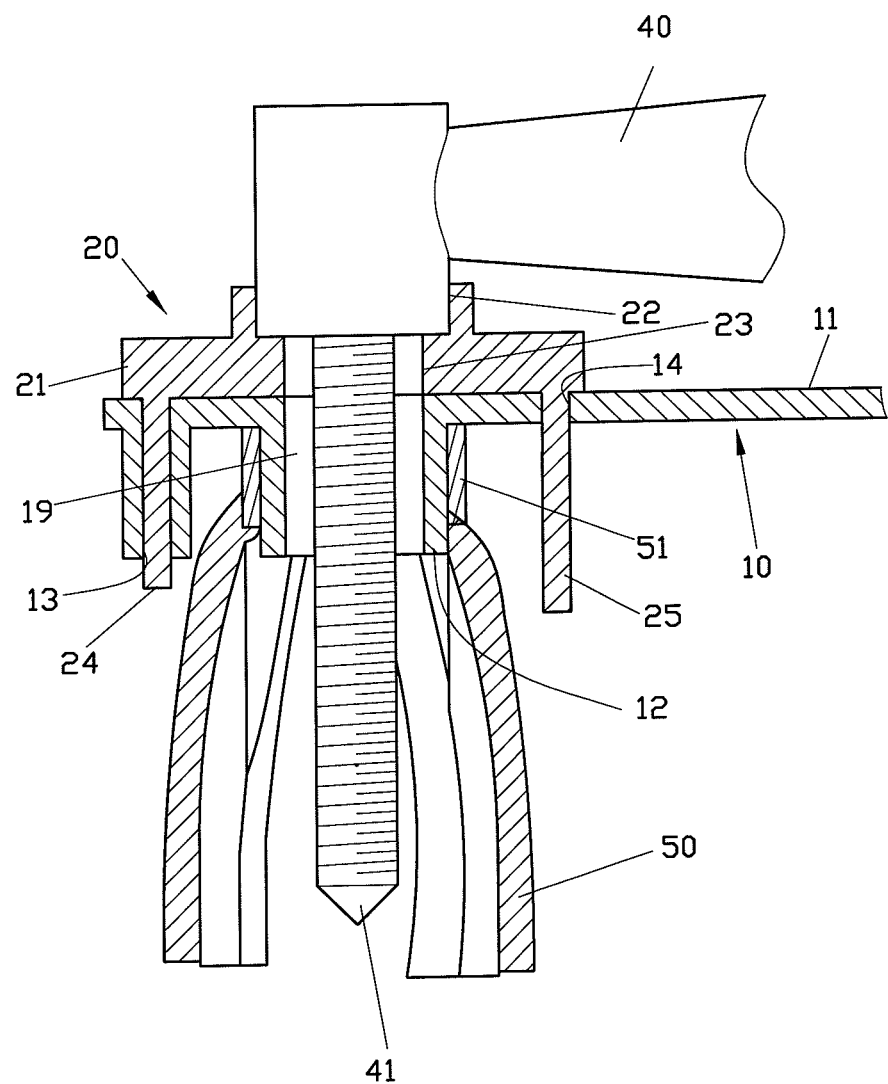
FIG. 7A is a section view showing an unused washer of the first preferred embodiment of the present invention.
Figure 7B:
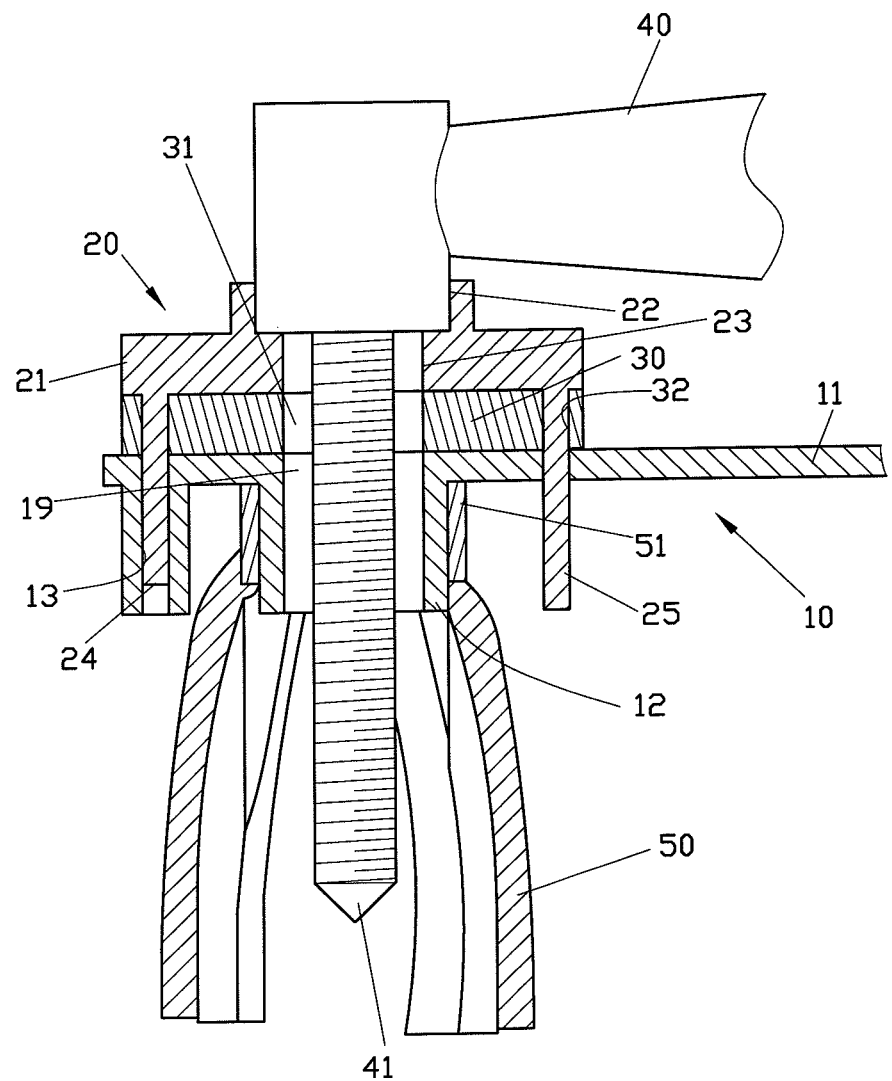
FIG. 7B is a section view showing a washer of the first preferred embodiment of the present invention in use.
Figure 7C:
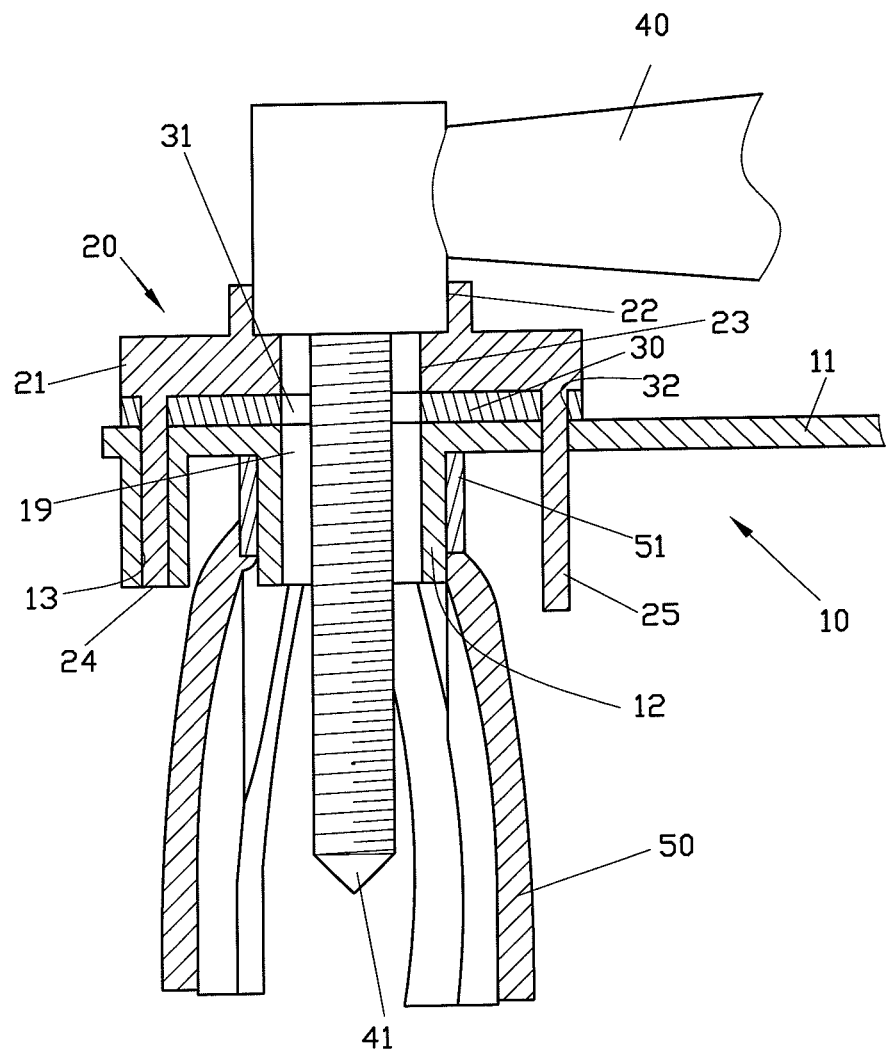
FIG. 7C is a section view showing another washer of the first preferred embodiment of the present invention in use.

A guiding seat 20 is disposed on the drilling apparatus 40 for assisting the drill 41 in inserting and positioning in the sleeve 12. The guiding seat 20 has a main body 21 which includes an assemble unit 22 and a first hole 23 defined on the assemble unit 22. A first guiding shank 24 and a second guiding shank 25 are disposed at two sides of the first hole 23. Wherein, the guiding seat 20 is installed on the drilling apparatus 40, and the drill 41 of the drilling apparatus 40 penetrates through the first hole 23. Furthermore, the first guiding shank 24 inserts into the guiding hole 13 of the guiding unit 11, and the second guiding shank 25 laterally passes the opening 15 and slides in the guiding slot 14 of the guiding unit 11; wherein, a length of the second guiding shank 25 is longer than a length of the first guiding shank 24. Preferably, the radius of the arc of the closed side of the guiding slot 14 is as the same as the radius of the second guiding shank 25 of the guiding seat 20. Referring to FIGS. 7A, 7B, and 7C, the dental implant guiding device comprises a washer 30; wherein, the washer 30 has a second hole 31 defined corresponding to the first hole 23 and two third holes 32 are defined at two sides of the first hole 31. When the first guiding shank 24 and the second guiding shank 25 of the guiding seat 20 are inserted into the corresponding third holes 32 and the washer 30 to the guiding seat 20 is assembled on the guiding seat 20, the user can choose the washer 30 with a proper thickness according to the drilling depth of the drill 41 in order to control the drilling depth.

Referring to FIG. 1, a prefabricated surgical guiding plate 50 is sleeved on the teeth of the patient, two guiding units 11 are pivotally connected by the combination unit 18. The sleeve 12 of the two guiding units 11 are respectively placed into the fixed sleeve 51 of the surgical guiding plate 50 so as to position the two guiding units 11 on the surgical guiding plate 50 without supporting. Referring to FIG. 4, when using a single guiding unit 11, the user inserts the sleeve 12 of the guiding unit 11 into the fixed sleeve 51 of the surgical guiding plate 50 and uses one hand to prop the shaft 16 of the guiding unit 11. Referring to FIG. 5, according to different places of the dental implant, the combination unit 18 can be adjusted to insert into the appropriate combination hole 17 of the two guiding units 11. Furthermore, the interval D between the guiding hole 13 of the guiding unit 11 and the guiding slot 14 is also adjustable so that the user chooses the appropriate guiding unit 11 according to the thickness of the patients' teeth ridge.

Figure 6A:
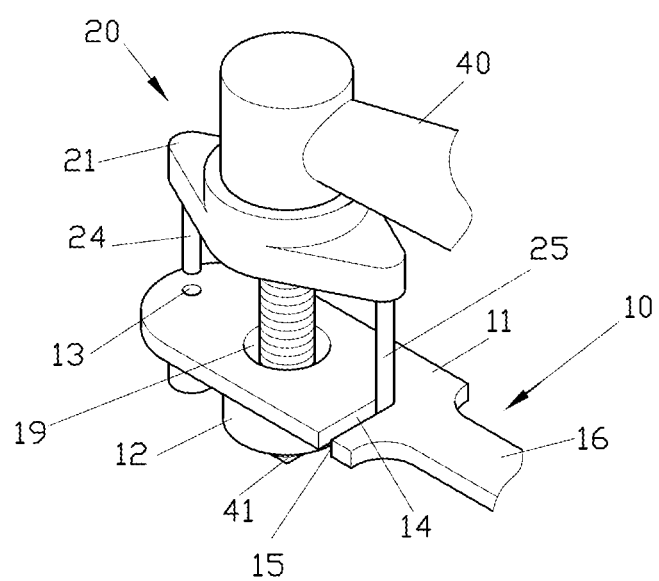
FIG. 6A is a schematic view showing the first preferred embodiment of the present invention in use.
Figure 6B:
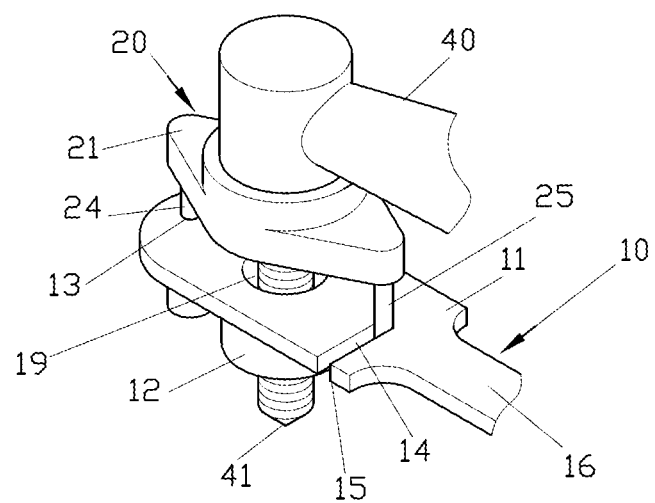
FIG. 6B is another schematic view showing the first preferred embodiment of the present invention in use.
Figure 6C:
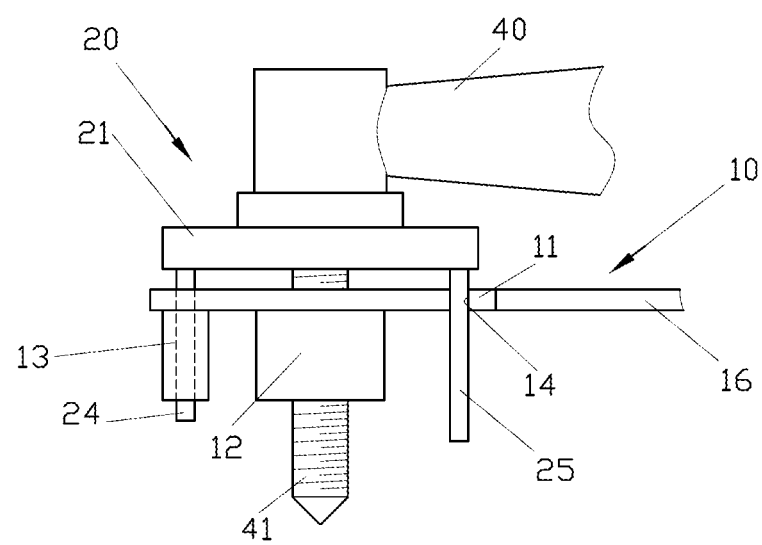
FIG. 6C is yet another schematic view showing the first preferred embodiment of the present invention in use.

Referring to FIGS. 6A to 6C, when drilling, the user initially passes the drill 41 of the drilling apparatus 40 through the first hole 23 of the guiding seat 20 so that the guiding seat 20 is sleeved on the drilling apparatus 40. Then, the user chooses the appropriate thickness of the washer 30 to install on the guiding seat 20 according to the pre-surgical evaluation so as to control the drilling depth of the drill 41. The user holds the drilling apparatus 40 and inserts the drill 41 into the cavity 19 of the sleeve 12 initially, then renders the longer second guiding shank 25 to laterally pass through the opening 15 and slide in the guiding slot 14 of the guiding unit 11 for the second guiding shank 25 to be positioned at the closed side of the guiding slot 14, and thence inserts the first guiding shank 24 into the corresponded guiding hole 13. When the first guiding shank 24 is inserted into the guiding hole 13, the guiding hole 13 restrains the first guiding shank 25 from being slanted. The arrangement of the guiding slot 14 as a straight slot prevents the guiding seat 20 from rotating about the first guiding shank 24 as the center so that the drill 41 is positioned in the cavity 19 of the sleeve 12. Wherein, the diameter of the cavity 19 of the sleeve 12 is greater than the diameter of the drill 41. Therefore, the sleeve 12 does not need to be replaced to fit the dimension of the drill 41. The drill 41 is firmly positioned without having the friction against the inner side of the sleeve 12.

To sum up, the cooperation of the guiding hole 13 and the guiding slot 14 of the guiding unit 11 with the first guiding shank 24 and the second guiding shank 25 of the guiding seat 20 allows the drill 41 to be rapidly positioned in the sleeve 12. After the first guiding shank 24 inserts into the guiding hole 13, the guiding hole 13 prevents the first guiding shank 24 from being slanted, and the guiding slot 14 prevents the guiding seat 20 from rotating so as to make the drill 41 be positioned at the center of the cavity 19 of the sleeve 12. The diameter of the cavity 19 is greater than the diameter of the drill 41 so that the guiding unit 11 does not need to be changed to adapt to different dimensions of the drills 41 in the surgery, which facilitates the reduction of the infection risks. Moreover, the drill 41 is positioned in the cavity 19 of the guiding unit 11 by the guiding seat 20, whereby the friction created between the drill 41 and the inner wall of the sleeve 12 of the guiding unit 11 is prevented to keep the apparatus from being broken and prevent the debris resulted from the friction from being dropped in the surgical area.

Furthermore, the different thicknesses of washers 30 are adjustable based on the demand to install on the guiding seat 20, facilitating the control of the drilling depth. The plurality of guiding units 11 of the guiding module 10 can be pivotally joined with each other by the combination unit 18, which also provide multiple choices of combination holes 17 so as to increases the suitability and application of the guiding module 10.

We claim:

1. A dental implant guiding device which is applied to guide a drill of a positioned drilling apparatus, said dental implant guiding device comprising:

a guiding module including at least one guiding unit; said guiding unit including a sleeve with a cavity, a guiding hole and a guiding slot; said guiding hole and said guiding slot being disposed at two opposite sides of said sleeve; said guiding slot being a straight slot extending from a near central portion of said guiding unit to a fringe of said guiding unit and thus forming an opening at said fringe of said guiding unit; and a guiding seat disposed on said drilling apparatus for allowing said drill to insert therethrough and fix on said sleeve; said guiding seat having a first hole defined thereon for a penetration of said drill; a first guiding shank disposed corresponding to said guiding hole and a second guiding shank disposed corresponding to said guiding slot being disposed at two sides of said first hole; a length of said second guiding shank being longer than a length of said first guiding shank.

2. The dental implant guiding device as claimed in claim 1, wherein said guiding slot has a first end being located at said near central portion of said guiding unit, said first end being in an arc shape, and a center of said arc-shaped first end of said guiding slot is aligned with centers of said sleeve and said guiding hole.

3. The dental implant guiding device as claimed in claim 1, wherein, a shaft is defined on said guiding unit, and said guiding slot is defined between said sleeve and said shaft; said guiding module has a plurality of guiding units, each of which forms at least one combination hole on said shaft so that a combination unit is inserted into said combination hole of said guiding units for pivotally joining said guiding units.

4. The dental implant guiding device as claimed in claim 1, wherein, said device comprises a washer with a second hole corresponding to said first hole, and said washer has two third holes defined at two sides of said second hole so that said first guiding shank and said second guiding shank of said guiding seat insert into said corresponding third holes respectively to install said washer on said guiding seat.

5. The dental implant guiding device as claimed in claim 1, wherein, said guiding module is disposed on a surgical guiding plate, and said guiding unit of said guiding module is fixed to said surgical guiding plate by placing said sleeve into a fixed sleeve of said surgical guiding plate.

\* \* \* \* \*